United States Patent
Ross et al.

(10) Patent No.: US 10,192,010 B1
(45) Date of Patent: Jan. 29, 2019

(54) SIMULATION OF CHEMICAL REACTIONS VIA MULTIPLE PROCESSING THREADS

(71) Applicant: X Development LLC, Mountain View, CA (US)

(72) Inventors: Jonathan Ross, Mountain View, CA (US); Jason Thompson, Redwood City, CA (US)

(73) Assignee: X Development LLC, Mountain View, CA (US)

( * ) Notice: Subject to any disclaimer, the term of this patent is extended or adjusted under 35 U.S.C. 154(b) by 255 days.

(21) Appl. No.: 15/164,125

(22) Filed: May 25, 2016

(51) Int. Cl.
G01N 33/48 (2006.01)
G01N 33/50 (2006.01)
G06F 17/50 (2006.01)
G06F 19/00 (2018.01)

(52) U.S. Cl.
CPC ........ G06F 17/5009 (2013.01); G06F 19/702 (2013.01)

(58) Field of Classification Search
None
See application file for complete search history.

(56) References Cited

U.S. PATENT DOCUMENTS

| | | | |
|---|---|---|---|
| 6,632,641 B1 | 10/2003 | Brennan et al. | |
| 7,072,028 B2 | 7/2006 | Powell et al. | |
| 7,769,576 B2 | 8/2010 | Paxson et al. | |
| 2003/0054430 A1* | 3/2003 | Korzekwa | C12Q 1/26 435/25 |
| 2007/0052705 A1* | 3/2007 | Oliveira | G06F 17/509 345/423 |

FOREIGN PATENT DOCUMENTS

| | | | |
|---|---|---|---|
| EP | 1725970 A2 | 11/2006 | |
| WO | WO1999050770 A1 | 10/1999 | |
| WO | WO 2002/063479 A1 * | 8/2002 | |

* cited by examiner

*Primary Examiner* — Russell S Negin

(74) *Attorney, Agent, or Firm* — Fenwick & West LLP

(57) ABSTRACT

An example method may include identifying (i) a first group of reactions that corresponds to a first set of precursors and a first set of reaction products and (ii) a second group of reactions that corresponds to a second set of precursors and a second set of reaction products. No precursor in the first set of precursors is also in the second set of precursors, no reaction product in the first set of reaction products is also a precursor in the second set of precursors, and no reaction product in the second set of reaction products is also a precursor in the first set of precursors. The method may also include executing a first processing thread to iteratively calculate respective quantities of the precursors in the first set of precursors and executing a second processing thread to iteratively calculate respective quantities of the precursors in the second set of precursors.

20 Claims, 9 Drawing Sheets

SIMULATION OF CHEMICAL REACTIONS VIA MULTIPLE PROCESSING THREADS

BACKGROUND

Unless otherwise indicated herein, the materials described in this section are not prior art to the claims in this application and are not admitted to be prior art by inclusion in this section.

Computing systems may be used to simulate the progress of one or more chemical reactions. In some cases, the progress of such chemical reactions may be mutually dependent due to the reactions having common reaction precursors.

SUMMARY

The time required to simulate the progress of multiple chemical reactions may be reduced by simulating the chemical reactions independently and contemporaneously. But in many cases of interest, one chemical reaction may share precursors with another reaction, or one reaction may yield a reaction product that is a precursor for another reaction. Reactions that share such dependencies can be simulated in concert to provide accurate results. However, as the simulation progresses, conditions may change such that one or more reactions can be accurately simulated independently of other reactions. For example, a first reaction may share a first precursor with a second reaction, and the second reaction may share a second precursor with a third reaction. The second reaction may also be dependent upon a third precursor. Upon exhaustion of the third precursor, the second reaction might no longer take place, thereby decoupling the first and third reactions. In such a situation, a computing system may simulate the first reaction and the third reaction independently (and possibly concurrently) via distinct processing threads. The processing threads may be executed by distinct processors of the same computing device or by respective processors of distinct computing devices.

In one example, a method includes identifying a first group of one or more chemical reactions and a second group of one or more chemical reactions. The first group of one or more chemical reactions may use a first set of one one or more precursors to produce a first set of one or more reaction products and the second group of one or more chemical reactions may use a second set of one or more precursors to produce a second set of one or more reaction products, such that (a) no precursor in the first set of one or more precursors is also in the second set of one or more precursors, (b) no reaction product in the first set of one or more reaction products is also a precursor in the second set of one or more precursors, and (c) no reaction product in the second set of one or more reaction products is also a precursor in the first set of one or more precursors. The method further includes, based on reaction kinetics of the one or more chemical reactions of the first group and initial respective quantities of the one or more precursors in the first set of one or more precursors, executing a first processing thread to iteratively calculate subsequent respective quantities of the one or more precursors in the first set of one or more precursors. The method further includes, based on reaction kinetics of the one or more chemical reactions of the second group and initial respective quantities of the one or more precursors in the second set of one or more precursors, executing a second processing thread to iteratively calculate subsequent respective quantities of the one or more precursors in the second set of one or more precursors.

In another example, one or more units of non-transitory computer readable media store instructions that, when executed by a computing system, cause the computing system to perform functions. The functions include identifying a first group of one or more chemical reactions and a second group of one or more chemical reactions. The first group of one or more chemical reactions may use a first set of one one or more precursors to produce a first set of one or more reaction products and the second group of one or more chemical reactions may use a second set of one or more precursors to produce a second set of one or more reaction products, such that (a) no precursor in the first set of one or more precursors is also in the second set of one or more precursors, (b) no reaction product in the first set of one or more reaction products is also a precursor in the second set of one or more precursors, and (c) no reaction product in the second set of one or more reaction products is also a precursor in the first set of one or more precursors. The functions further include, based on reaction kinetics of the one or more chemical reactions of the first group and initial respective quantities of the one or more precursors in the first set of one or more precursors, executing a first processing thread to iteratively calculate subsequent respective quantities of the one or more precursors in the first set of one or more precursors. The functions further include, based on reaction kinetics of the one or more chemical reactions of the second group and initial respective quantities of the one or more precursors in the second set of one or more precursors, executing a second processing thread to iteratively calculate subsequent respective quantities of the one or more precursors in the second set of one or more precursors.

In yet another example, a computing system includes one or more processors and one or more memory units storing instructions that, when executed by the one or more processors, cause the computing system to perform functions. The functions include identifying a first group of one or more chemical reactions and a second group of one or more chemical reactions. The first group of one or more chemical reactions may use a first set of one one or more precursors to produce a first set of one or more reaction products and the second group of one or more chemical reactions may use a second set of one or more precursors to produce a second set of one or more reaction products, such that (a) no precursor in the first set of one or more precursors is also in the second set of one or more precursors, (b) no reaction product in the first set of one or more reaction products is also a precursor in the second set of one or more precursors, and (c) no reaction product in the second set of one or more reaction products is also a precursor in the first set of one or more precursors. The functions further include, based on reaction kinetics of the one or more chemical reactions of the first group and initial respective quantities of the one or more precursors in the first set of one or more precursors, executing a first processing thread to iteratively calculate subsequent respective quantities of the one or more precursors in the first set of one or more precursors. The functions further include, based on reaction kinetics of the one or more chemical reactions of the second group and initial respective quantities of the one or more precursors in the second set of one or more precursors, executing a second processing thread to iteratively calculate subsequent respective quantities of the one or more precursors in the second set of one or more precursors.

In yet another example, a computing system includes means for identifying a first group of one or more chemical reactions and a second group of one or more chemical reactions. The first group of one or more chemical reactions may use a first set of one or more precursors to produce a first set of one or more reaction products and the second group of one or more chemical reactions may use a second set of one or more precursors to produce a second set of one or more reaction products, such that (a) no precursor in the first set of one or more precursors is also in the second set of one or more precursors, (b) no reaction product in the first set of one or more reaction products is also a precursor in the second set of one or more precursors, and (c) no reaction product in the second set of one or more reaction products is also a precursor in the first set of one or more precursors. The computing system further includes means for, based on reaction kinetics of the one or more chemical reactions of the first group and initial respective quantities of the one or more precursors in the first set of one or more precursors, executing a first processing thread to iteratively calculate subsequent respective quantities of the one or more precursors in the first set of one or more precursors. The computing system further includes means for, based on reaction kinetics of the one or more chemical reactions of the second group and initial respective quantities of the one or more precursors in the second set of one or more precursors, executing a second processing thread to iteratively calculate subsequent respective quantities of the one or more precursors in the second set of one or more precursors.

These as well as other aspects, advantages, and alternatives, will become apparent to those of ordinary skill in the art by reading the following detailed description, with reference where appropriate to the accompanying drawings.

DETAILED DESCRIPTION

Figure 1:
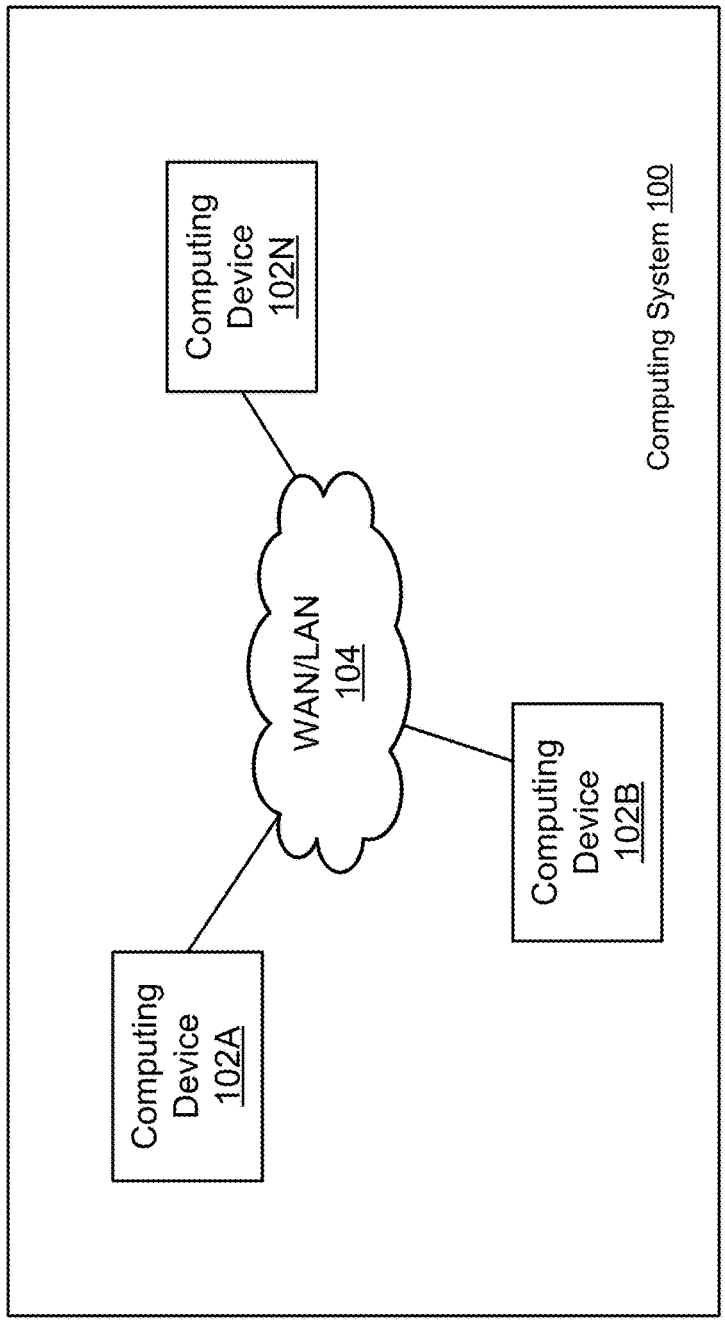
FIG. 1 depicts a computing system, according to an example embodiment.

Example methods and systems are described herein. Any example implementation or feature described herein is not necessarily to be construed as preferred or advantageous over other implementations or features. The example implementations described herein are not meant to be limiting. Certain aspects of the disclosed methods and systems can be arranged and combined in a wide variety of different configurations, all of which are contemplated herein.

Furthermore, the particular arrangements shown in the Figures should not be viewed as limiting. It should be understood that other embodiments might include more or fewer of each element shown in a given Figure. Further, some of the illustrated elements may be combined or omitted. Yet further, an example embodiment may include elements that are not illustrated in the Figures.

In some situations, it may be useful to simulate the progress of multiple chemical reactions occurring within a common environment. Such simulated reactions may be related to DNA transcription or cellular metabolism, for example. The time required to perform the simulation may be reduced by simulating the chemical reactions independently and contemporaneously. But in many cases of interest, one chemical reaction may share precursors with another reaction, or one reaction may yield a reaction product that is a precursor for another reaction. Reactions that share such dependencies can be simulated in concert to provide accurate results.

For instance, a first reaction and a second reaction may share a first precursor, meaning that the rate at which the first reaction uses the first precursor may affect the rate at which the second reaction uses the first precursor. In this context, a reaction "using" a precursor may include the reaction consuming a precursor metabolite or using an enzyme to facilitate the reaction, for example. Similarly, the rate at which the second reaction uses the first precursor may affect the rate at which the first reaction uses the first precursor. As a result, accuracy can be achieved by simulating the progress of the first and second reactions in concert. For example, a computing system may perform the simulation of the first and second reactions via execution of a single processing thread.

Additionally, the second reaction may share a second precursor with a third reaction. In this case, the rate at which the third reaction uses the second precursor may affect the rate at which the second reaction uses the second precursor, which in turn may affect the rate at which the second reaction uses the first precursor. As mentioned above, this may affect the rate at which the first reaction uses the first precursor. Consequently, the first, second, and third reactions may be simulated in concert via execution of a single processing thread.

As explained above, one or more interdependent reactions can be simulated in concert to yield accurate results. However, as the simulation progresses, conditions may change such that one or more reactions can be accurately simulated independently of other reactions. For example, the second reaction may also use a third precursor. If, according to the simulation, the third precursor were exhausted, the second reaction could no longer take place. This would decouple the first and third reactions such that the third reaction could be simulated independently of the first reaction. In such a situation, the computing system may simulate the first reaction and the third reaction independently (and possibly concurrently) via distinct processing threads. The processing threads may be executed by distinct processors of the same computing device or by respective processors of distinct computing devices.

Reference will now be made in detail to various embodiments, examples of which are illustrated in the accompanying drawings. In the following detailed description, numerous specific details are set forth in order to provide a thorough understanding of the present disclosure and the described embodiments. However, the present disclosure may be practiced without these specific details. In other instances, well-known methods, procedures, components, and circuits have not been described in detail so as not to unnecessarily obscure aspects of the embodiments.

FIG. 1 depicts a computing system 100. The computing system 100 may include a computing device 102A, a computing device 102B, and a computing device 102N. Although the computing system 100 is depicted as including three computing devices, the computing system 100 may include any number of computing devices similar to the computing devices 102A, 102B, or 102N. The computing devices 102A-N may take the form of desktop computers, laptop computers, tablet computers, smartphones, or servers (e.g., "cloud computing systems"). Other examples are possible.

The computing devices 102A-N may be communicatively coupled via a wide-area network and/or a local-area network (WAN/LAN) 104. The computing devices 102A-N may each include a wired and/or wireless communication interface configured to send and/or receive communication signals via the WAN/LAN 104. The communication interfaces of the computing devices 102A-N are discussed in more detail below. The WAN/LAN 104 may include any number of switches, cables, routers, repeaters, or other components configured to facilitate wired and/or wireless communication between any of the computing devices 102A-N.

Figure 2:
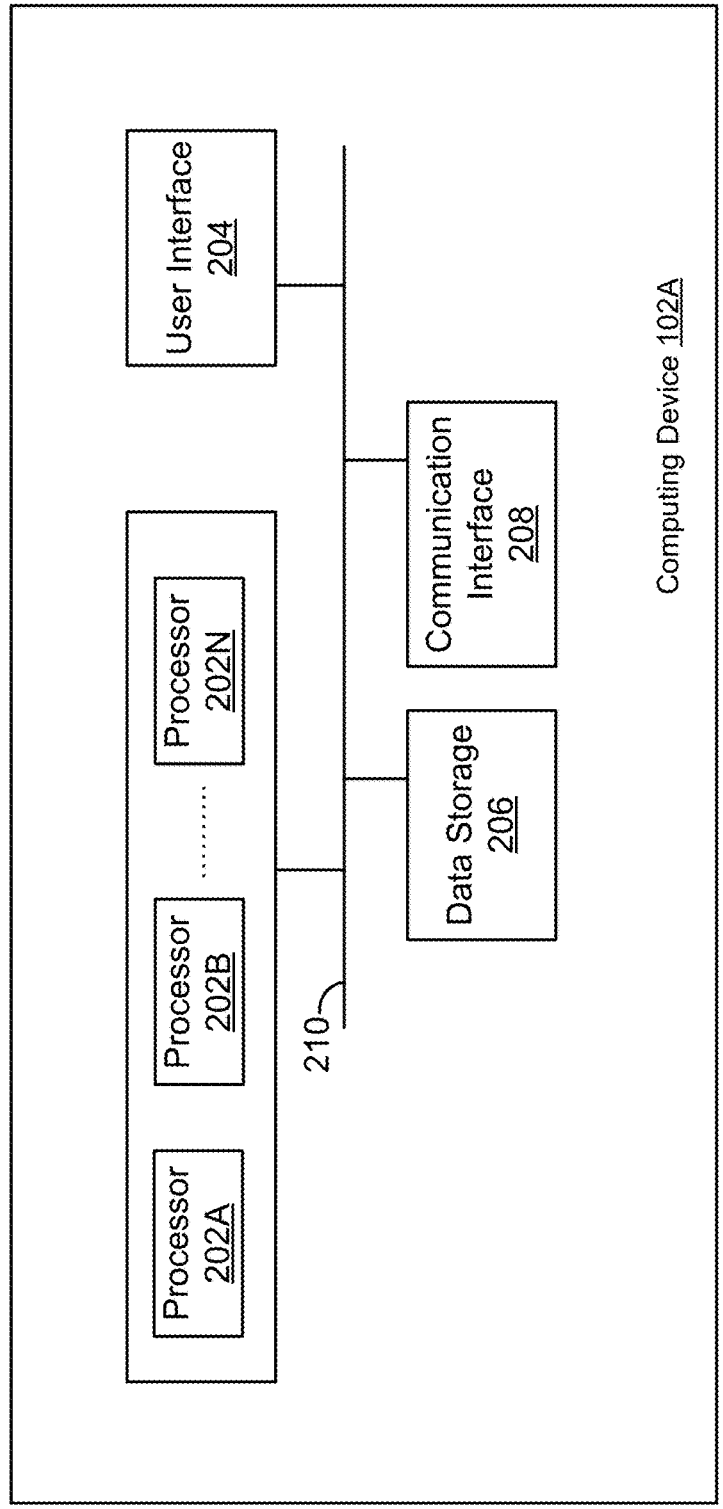
FIG. 2 depicts a computing device, according to an example embodiment.

FIG. 2 depicts the computing device 102A. The computing device 102A may include processors 202A, 202B, and 202N, a user interface 204, data storage 206, and a communication interface 208, all of which may be communicatively linked to each other via a bus 210.

The processors 202A-N may each include a general purpose processor (e.g., a microprocessor) and/or a special purpose processor (e.g., a digital signal processor (DSP)).

The user interface 204 may enable interaction between a user (if applicable) and the computing device 102A. As such, the user interface 204 may include input components such as a keyboard, a keypad, a mouse, a touch-sensitive panel, a microphone, and/or a camera. The user interface 204 may also include output components such as a display screen (which, for example, may be combined with a touch-sensitive panel), a audio speaker, and/or a haptic feedback system.

Data storage 206 may include one or more memory components that are volatile, nonvolatile, removable, and/or non-removable. Such components could be magnetic, optical, or flash storage, and may be integrated with one or more of the processors 202A-N. Further, data storage 206 may take the form of a non-transitory computer readable storage medium, having stored thereon program instructions that, when executed by one or more of the processors 202A-N, cause the computing device 102A to perform one or more functions described herein. Data storage 206 may also store other types of information or data, such as those types described herein.

The communication interface 208 may include one or more wireless interfaces and/or one or more wired interfaces which allow the computing device 102A to communicate via one or more networks, such as WAN/LAN 104. Such wireless interfaces may provide for communication under one or more wireless communication protocols, such as Bluetooth, WiFi (e.g., an IEEE 802.11 protocol), Long-Term Evolution (LTE), WiMAX (e.g., an IEEE 802.16 standard), a radio-frequency ID (RFID) protocol, near-field communication (NFC), and/or other wireless communication protocols. Such wired interfaces may include an Ethernet interface, a Universal Serial Bus (USB) interface, or a similar interface to communicate via a wire, a twisted pair of wires, a coaxial cable, an optical link, a fiber-optic link, or another physical connection to a wired or wireless network. The computing device 102A may communicate with the computing devices 102B and 102N (or other computing devices), and/or other entities via the communication interface 208.

Figure 3:
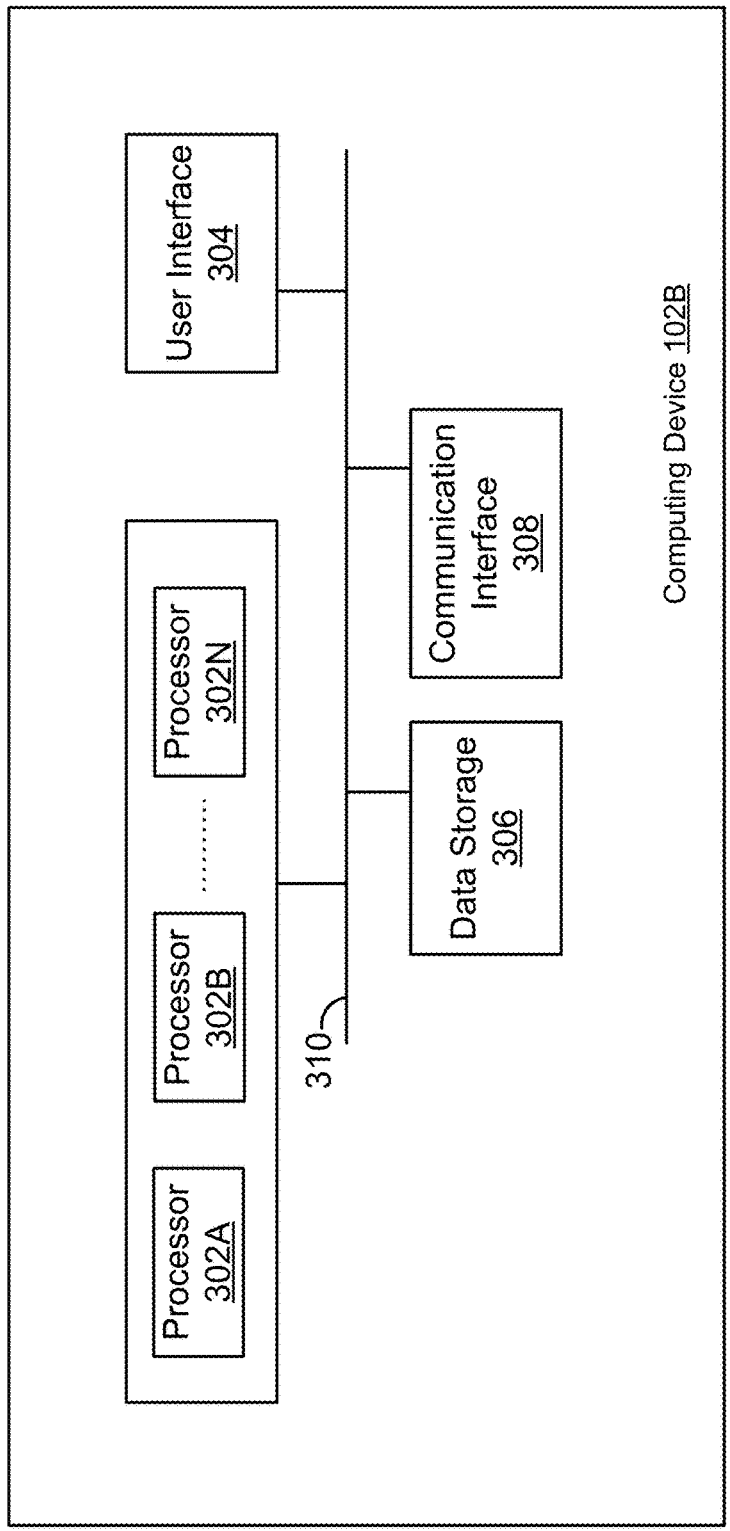
FIG. 3 depicts another computing device, according to an example embodiment.

FIG. 3 depicts the computing device 102B. The computing device 102B may include processors 302A, 302B, and 302N, a user interface 304, data storage 306, and a communication interface 308, all of which may be communicatively linked to each other via a bus 310.

The processors 302A, 302B, and 302N, the user interface 304, data storage 306, and the communication interface 308 may have similar characteristics as, and function similarly to, the respective processors 202A, 202B, and 202N, the user interface 204, data storage 206, and the communication interface 208.

Figure 4:
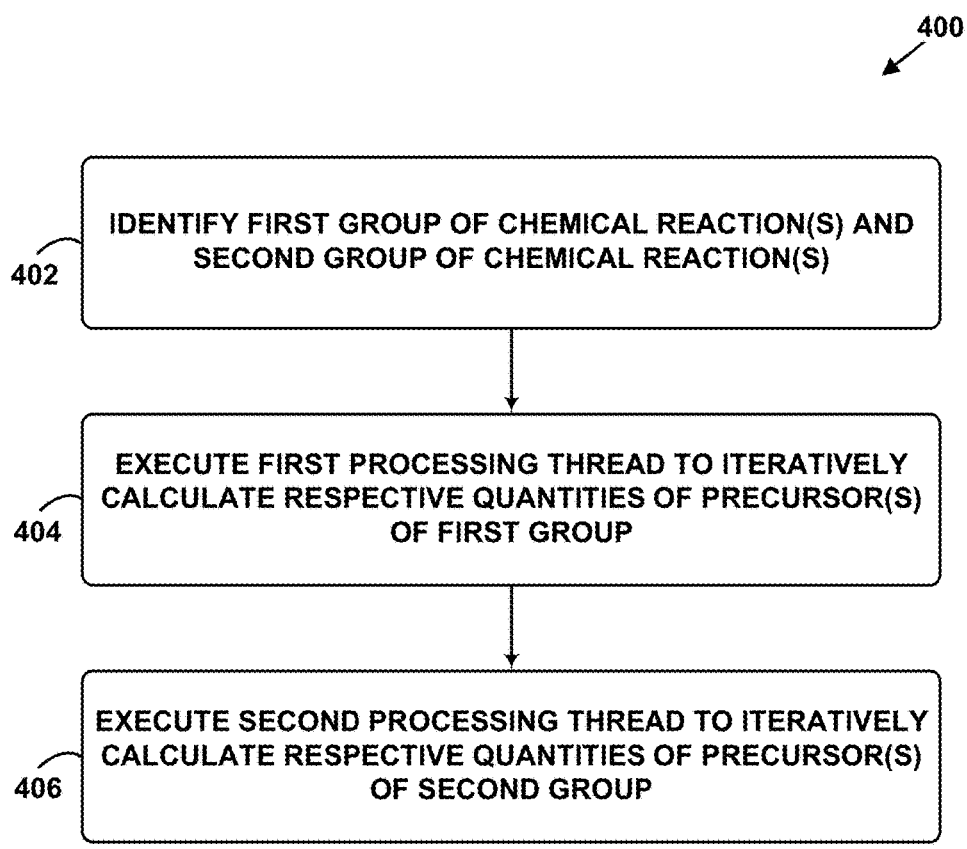
FIG. 4 is a block diagram of a method, according to an example embodiment.

Method 400 depicted in FIG. 4 presents an example method that can be performed by the computing system 100, including one or more of the computing devices 102A-N. In other examples, the method 400 may be performed by any combination of one or more suitable components described herein. FIG. 4 may include one or more operations, functions, or actions as illustrated by one or more of blocks 402, 404, and 406. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 400, and other processes and methods disclosed herein, the flowcharts show functionality and operation of one possible implementation of present embodiments. In this regard, each block may represent a module, a segment, or a portion of program code, which includes one or more instructions executable by a processor for implementing specific logical functions or steps in a process. The program code may be stored on any type of computer readable medium, for example, such as a storage device including a disk or hard drive. The computer readable medium may include a non-transitory computer readable medium, for example, such as computer readable media that stores data for short periods of time like register memory, processor cache, or Random Access Memory (RAM). The computer readable medium may also include non-transitory media, such as secondary or persistent long term storage, like read-only memory (ROM), optical or magnetic disks, or compact-disc read-only memory (CD-ROM), for example. The computer readable media may also be any other volatile or non-volatile storage system. The computer readable medium may be considered a computer readable storage medium, a tangible storage device, or other article of manufacture, for example.

In addition, for the method 400, and other processes and methods disclosed herein, each block in FIG. 4 may represent circuitry that is wired to perform the specific logical functions in the process. For example, one or more field-programmable gate arrays (FPGA) and/or one or more application-specific integrated circuits (ASIC) might be configured to perform the method 400 and/or other processes and methods disclosed herein.

Figure 5:
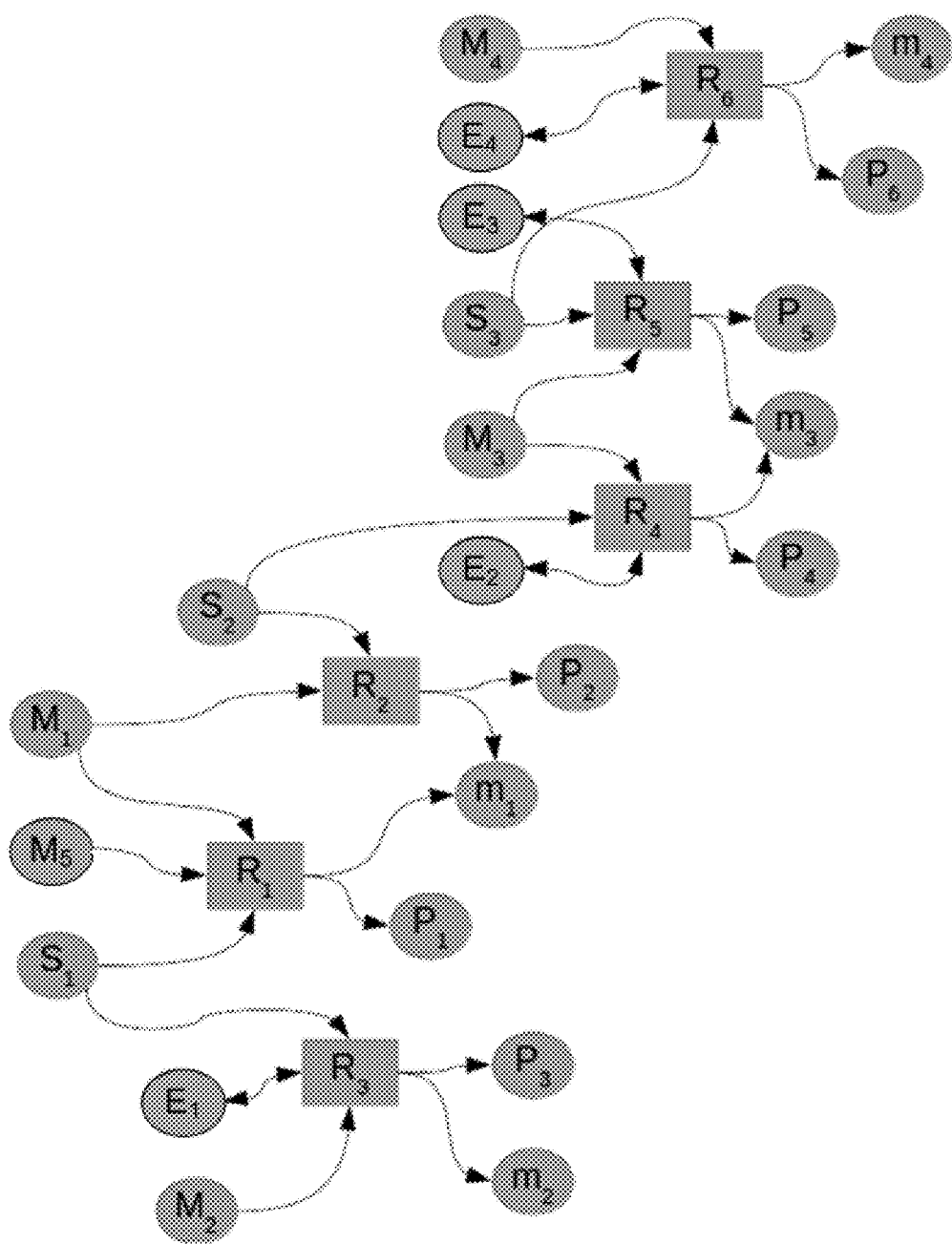
FIG. 5 is a schematic diagram of chemical reactions, according to an example embodiment.

The computing system 100 may perform the method 400, which may be related to a simulation of chemical reactions. Referring to FIG. 5, for example, the simulated chemical reactions may include $R_1$, $R_2$, $R_3$, $R_4$, $R_5$, and $R_6$. The simulation may also involve precursor metabolites $M_1$, $M_2$, $M_3$, $M_4$, and $M_5$, substrates $S_1$, $S_2$, and $S_3$, enzymes $E_1$, $E_2$, $E_3$, and $E_4$, spent metabolites $m_1$, $m_2$, $m_3$, and $m_4$, and reaction products $P_1$, $P_2$, $P_3$, $P_4$, $P_5$, and $P_6$.

Generally, the reactions consume the precursor metabolites and substrates, but do not consume the enzymes. For example, each occurrence of $R_3$ decrements the available quantity of $M_2$ and $S_1$, but does not affect the available quantity of $E_1$. Hereinafter, precursor metabolites $M_1$, $M_2$, $M_3$, $M_4$, and $M_5$, substrates $S_1$, $S_2$, and $S_3$, and enzymes $E_1$, $E_2$, $E_3$, and $E_4$ may generally be referred to as "precursors" in that they can interact to facilitate one or more of the chemical reactions $R_1$, $R_2$, $R_3$, $R_4$, $R_5$, and $R_6$. In a similar manner, spent metabolites $m_1$, $m_2$, $m_3$, and $m_4$ and reaction products $P_1$, $P_2$, $P_3$, $P_4$, $P_5$, and $P_6$ may all be referred to as "reaction products" in that instances of spent metabolites $m_1$, $m_2$, $m_3$, and $m_4$ and instances of reaction products $P_1$, $P_2$, $P_3$, $P_4$, $P_5$, and $P_6$ are "produced" by at least one of the chemical reactions $R_1$, $R_2$, $R_3$, $R_4$, $R_5$, and $R_6$.

As shown in FIG. 5, the progress of reactions $R_1$, $R_2$, $R_3$, $R_4$, $R_5$, and $R_6$ may be mutually dependent due to "sharing" of precursors. For example, $R_3$ may be dependent on $R_1$ because they share $S_1$ as a precursor. $R_1$ may be dependent on $R_2$ because they share $M_1$ as a precursor. Also, $R_2$ may be dependent on $R_4$ because they share $S_2$ as a precursor. Additionally, $R_4$ may be dependent on $R_5$ because they share $M_3$ as a precursor. Also, $R_5$ may be dependent on $R_6$ because they share $S_3$ as a precursor. Generally, a transitive property exists such that if a first reaction shares a first precursor with a second reaction, and the second reaction shares a second precursor with a third reaction, then the first reaction and the third reaction may be mutually dependent. In some examples that are not shown in FIG. 5, a first reaction might be dependent on a second reaction because the second reaction yields a reaction product that is a precursor of the first reaction.

As long as the reactions $R_1$, $R_2$, $R_3$, $R_4$, $R_5$, and $R_6$ are mutually dependent for any of the reasons listed (or not listed) above, the computing system 100 may continue to simulate the progress of the reactions $R_1$, $R_2$, $R_3$, $R_4$, $R_5$, and $R_6$ as a single group such that the effects of each reaction of the group on each of the other reactions of the group are accounted for. For example, the computing system 100 may execute instructions of a single processing thread to simulate the reactions $R_1$, $R_2$, $R_3$, $R_4$, $R_5$, and $R_6$. As is known in the art, a processing thread may include a set of multiple instructions that are to be executed sequentially. In some other contrasting examples that are described below, the computing system 100 may execute multiple independent processing threads, perhaps contemporaneously, to simulate the progress of one or more of the reactions $R_1$, $R_2$, $R_3$, $R_4$, $R_5$, and $R_6$.

Accordingly, at block 402 the method 400 includes identifying a first group of one or more chemical reactions and a second group of one or more chemical reactions. As the simulation performed by the computing system 100 progresses, certain precursors may become completely or substantially consumed by one or more of the reactions $R_1$, $R_2$, $R_3$, $R_4$, $R_5$, and $R_6$. For example, the reactions $R_4$ and $R_5$ may progress such that the quantity of the precursor $M_3$ becomes zero or close enough to zero so as to be negligible. This is denoted in FIG. 6 by an "X" over $M_3$. The absence of $M_3$ might prevent the reactions $R_4$ and $R_5$ from occurring. As such, reactions $R_4$ and $R_5$ are also marked by an "X" in FIG. 6. The computing system 100 may evaluate the simulation at periodic and/or non-periodic intervals to determine whether conditions such as a depleted precursor allow the simulation to be bifurcated into one or more independent simulations that can be executed contemporaneously. As long as the reactions $R_4$ and $R_5$ are no longer occurring (e.g., due to the absence of precursor $M_3$), the computing system 100 may divide the reactions into a first group and a second group.

Figure 6:
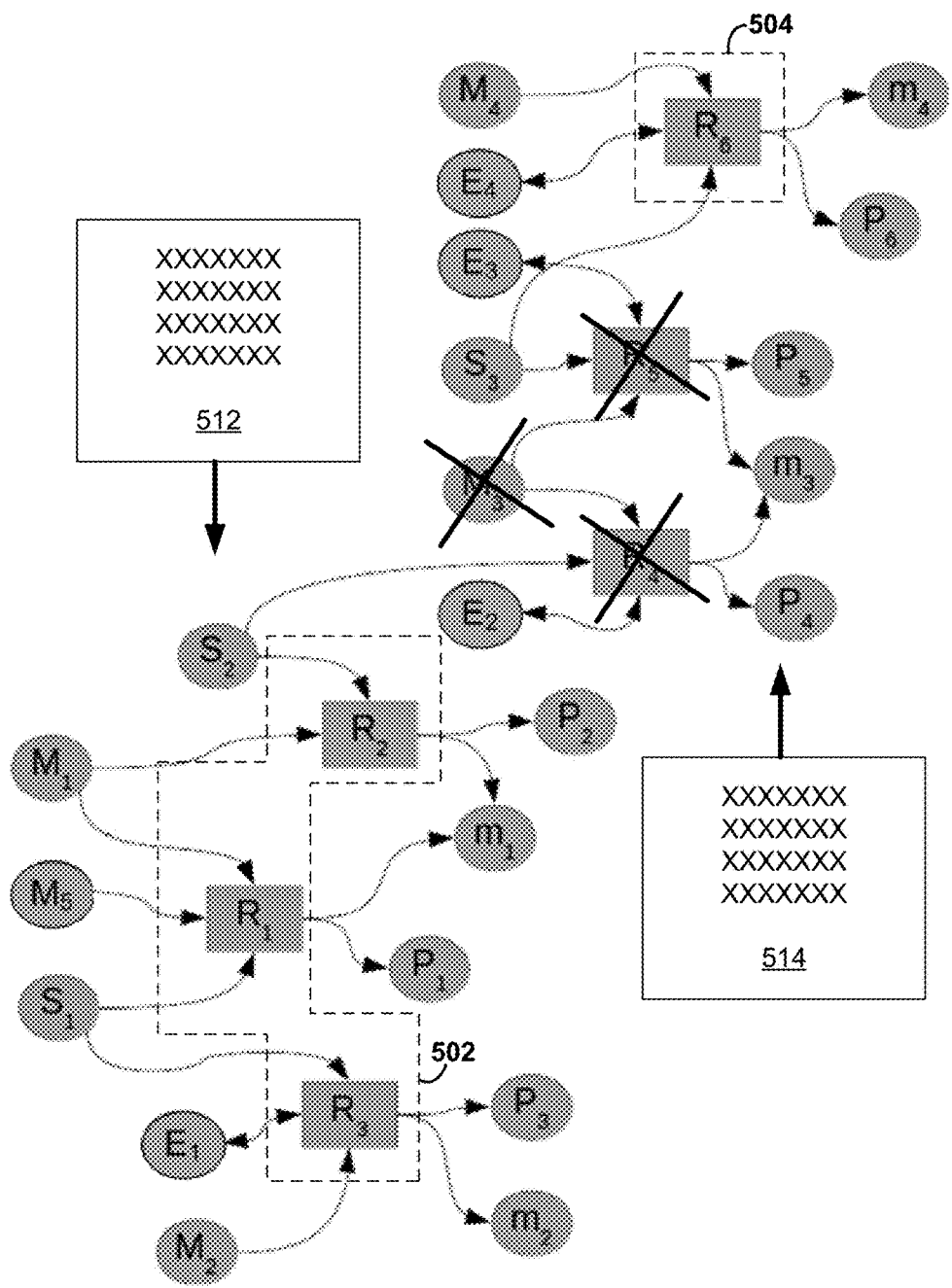
FIG. 6 is a schematic diagram of two groups of chemical reactions and two respective processing threads, according to an example embodiment.

In the example of FIG. 6, the group 502 may include the reactions $R_1$, $R_2$, and $R_3$, and the group 504 may include the reaction $R_6$. The group 502 may use a first set of precursors comprising $M_2$, $E_1$, $S_1$, $M_5$, $M_1$, and $S_2$. The group 502 may also produce a first set of reaction products comprising $m_2$, $P_3$, $P_1$, $m_1$, and $P_2$. The group 504 may use a second set of precursors comprising $S_3$, $E_4$, and $M_4$. The group 504 may also produce a second set of reaction products comprising $m_4$ and $P_6$.

The computing system 100 may identify the group 502 and the group 504 as being suitable for independent simulation because the group 502 and the group 504 do not share any precursors, no reaction product of the group 502 is a precursor of the group 504, and no reaction product of the group 504 is a precursor of the group 502.

At block 404, the method 400 includes executing a first processing thread to iteratively calculate, based on reaction kinetics of the reactions of the first group of reactions and initial respective quantities of the precursors in the first set of precursors, subsequent respective quantities of the precursors in the first set of precursors. For example, the computing system 100 may use initial respective quantities of the precursors $M_2$, $E_1$, $S_1$, $M_5$, $M_1$, and $S_2$ to execute the first processing thread 512 to iteratively calculate subsequent respective quantities of the precursors $M_2$, $E_1$, $S_1$, $M_5$, $M_1$, and $S_2$. In addition, the computing system 100 may use initial respective quantities of the reaction products $m_2$, $P_3$, $P_1$, $m_1$, and $P_2$ to execute the first processing thread 512 to iteratively calculate subsequent respective quantities of the reaction products $m_2$, $P_3$, $P_1$, $m_1$, and $P_2$.

For example, the computing system 100 might execute the first processing thread 512 to assign the reaction $R_3$ a probability $p_3$ that the reaction $R_3$ will occur during a given instance of time. $p_3$ may be determined based on respective initial quantities of the precursors $E_1$, $M_2$, and $S_1$, for example. The computing system 100 might also assign the reaction $R_1$ a probability $p_1$ that the reaction $R_1$ will occur during the given instance of time. $p_1$ may be determined based on respective initial quantities of the precursors $S_1$, $M_5$, and $M_1$, for example. The computing system 100 might also assign the reaction $R_2$ a probability $p_2$ that the reaction $R_2$ will occur during the given instance of time. $p_2$ may be determined based on respective initial quantities of the precursors $M_1$ and $S_2$, for example. The probabilities $p_3$, $p_1$, and $p_2$ may be normalized such that the sum of $p_3$, $p_1$, and $p_2$ is equal to 1. The computing system 100 may then use a randomly generated number to determine which of the reactions $R_3$, $R_1$, and $R_2$ occurs next. The computing system 100 may then update the quantities of the appropriate precursors and reaction products according to the reaction that was determined to occur next, and repeat this process one or more times.

In another example, the computing system 100 might execute the first processing thread 512 to determine respective reaction rates for the reactions of the group 502. For example, the computing system 100 may assign a rate $r_3$ to the reaction $R_3$ based on reaction kinetics of the reaction $R_3$ and initial respective quantities of the precursors $M_2$, $E_1$, and $S_1$. Additionally, the computing system 100 may assign a rate $r_1$ to the reaction $R_1$ based on reaction kinetics of the reaction $R_1$ and initial respective quantities of the precursors $S_1$, $M_5$, and $M_1$. Also, the computing system 100 may assign a rate $r_2$ to the reaction $R_2$ based on reaction kinetics of the reaction $R_2$ and initial respective quantities of the precursors $M_1$ and $S_2$. The computing system 100 may simulate the reactions of the group 502 as occurring contemporaneously according to their respective reaction rates. The computing system 100 may iteratively update the quantities of the precursors $M_2$, $E_1$, $S_1$, $M_5$, $M_1$, $S_2$ and the reaction products $m_2$, $P_3$, $P_1$, $m_1$, and $P_2$ as appropriate.

At block 406, the method 400 includes executing a second processing thread to iteratively calculate, based on reaction kinetics of the reactions of the second group of reactions and initial respective quantities of the precursors in the second set of precursors, subsequent respective quantities of the precursors in the second set of precursors. For example, the computing system 100 may use initial respective quantities of the precursors $S_3$, $E_4$, and $M_4$ to execute the second processing thread 514 to iteratively calculate subsequent respective quantities of the precursors $S_3$, $E_4$, and $M_4$. In addition, the computing system 100 may use initial respective quantities of the reaction products $P_6$ and $m_4$ to execute the second processing thread 514 to iteratively calculate subsequent respective quantities of the reaction products $P_6$ and $m_4$.

The computing system 100 may execute the second processing thread 514 to calculate the subsequent respective quantities of the precursors $S_3$, $E_4$, and $M_4$ and the reaction products $P_6$ and $m_4$ in any manner described above with regard to block 404.

Prior to executing the first processing thread 512 and the second processing thread 514 and to initialize the simulation, the computing system 100 may receive input indicating the initial respective quantities of the precursors $M_1$, $M_2$, $M_3$, $M_4$, $M_5$, $S_1$, $S_2$, $S_3$, $E_1$, $E_2$, $E_3$, and $E_4$. The input may be received via user interface 204 or user interface 304, for example.

In some examples, the computing device 102A may execute both the first processing thread 512 and the second processing thread 514. More specifically, the processor 202A may execute the first processing thread 512 and the processor 202B may execute the second processing thread 514.

In another example, the computing device 102A may execute the first processing thread 512 and the computing device 102B may execute the second processing thread 514. More specifically, the processor 202A may execute the first processing thread 512 and the processor 302A may execute the second processing thread 514.

In yet another example, the computing device 102A may execute both the first processing thread 512 and the second processing thread 514. More specifically, the processor 202A may execute both the first processing thread 512 and the second processing thread 514 via time slicing or similar techniques.

Figure 7:
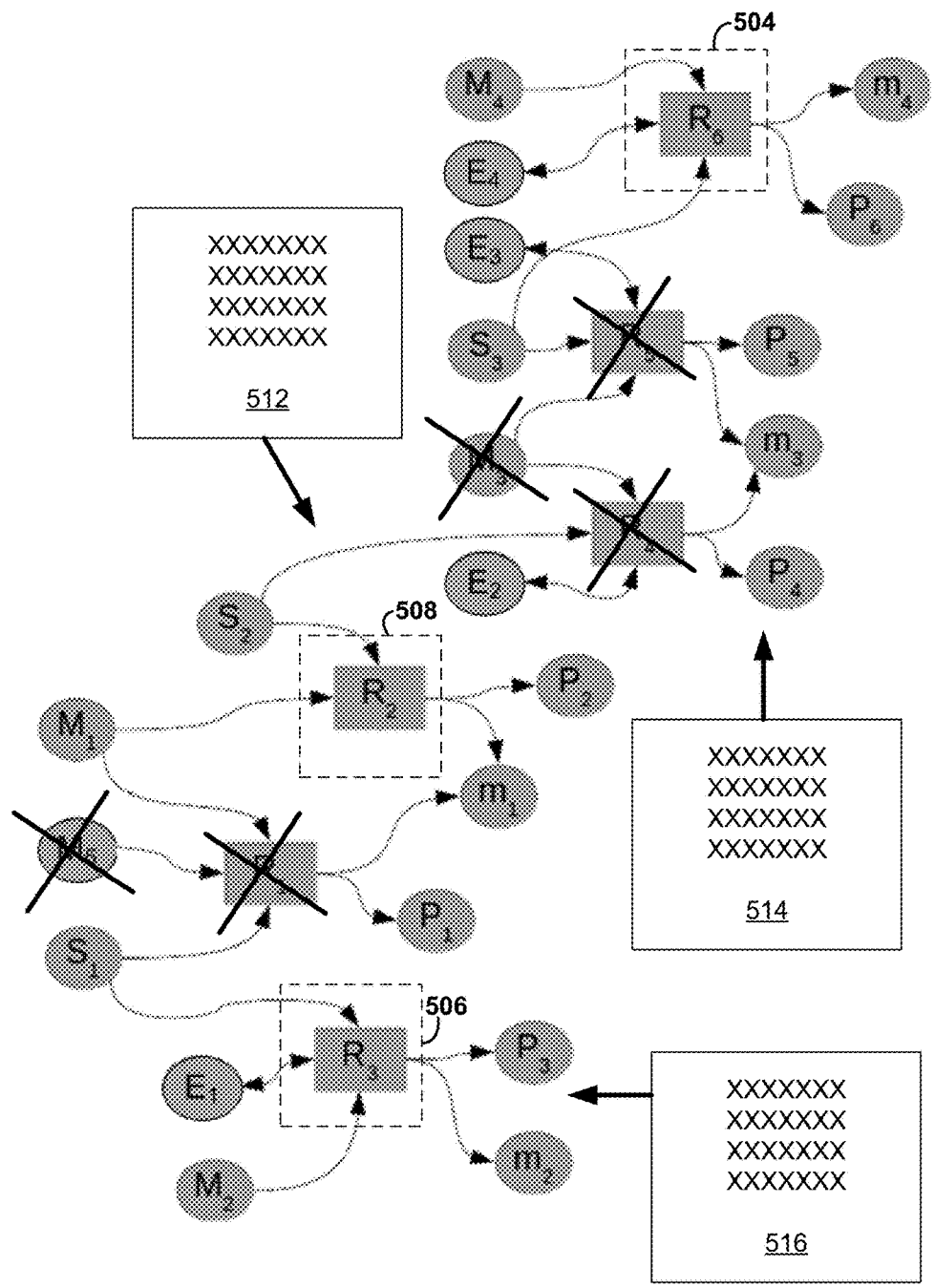
FIG. 7 is a schematic diagram of three groups of chemical reactions and three respective processing threads, according to an example embodiment.

As shown in FIG. 7, the computing system 100 may also execute a third processing thread 516. For instance, the computing system 100 may execute the first processing thread 512 to a point at which the precursor $M_5$ is also exhausted (or substantially exhausted) in addition to $M_3$. The computing system 100 may determine that the group 502 may be further bifurcated into a group 506 that includes $R_3$ and a group 508 that includes $R_2$. The computing system 100 may then initiate executing the third processing thread 516 to continue simulating the progress of the reaction $R_3$. Similarly, the computing system 100 may continue executing the first processing thread 512 (or perhaps a new fourth processing thread) to further simulate the progress of reaction $R_2$. In addition, the computing system 100 may continue executing the processing thread 514 to further simulate the progress of reaction $R_6$.

In some cases, precursors may reemerge within the simulation after they have been exhausted. For example, a new precursor (not shown) might be introduced into the simulation, causing a new reaction (not shown) to take place, which may generate the precursor $M_3$ within the simulation after $M_3$ was temporarily exhausted. This may occur for numerous other reasons that are not discussed herein.

In some examples, each of the processing threads 512, 514, and 516 may include instructions that cause the computing system 100 to monitor for the reemergence of $M_5$, for example. If the reemergence of $M_5$ is detected, the computing system 100 may combine the functions of the processing thread 512 and the processing thread 516 into a single new processing thread that simulates the reactions $R_1$, $R_2$, and $R_3$ while accounting for their reemerged mutual dependence.

In examples where three or more processing threads are executed by the computing system 100, the three or more processing threads may executed by a single processor of the computing system, two processors of a single computing device, two processors of distinct computing devices, or three or more processors of one or more computing devices. Other examples are possible.

Figure 8:
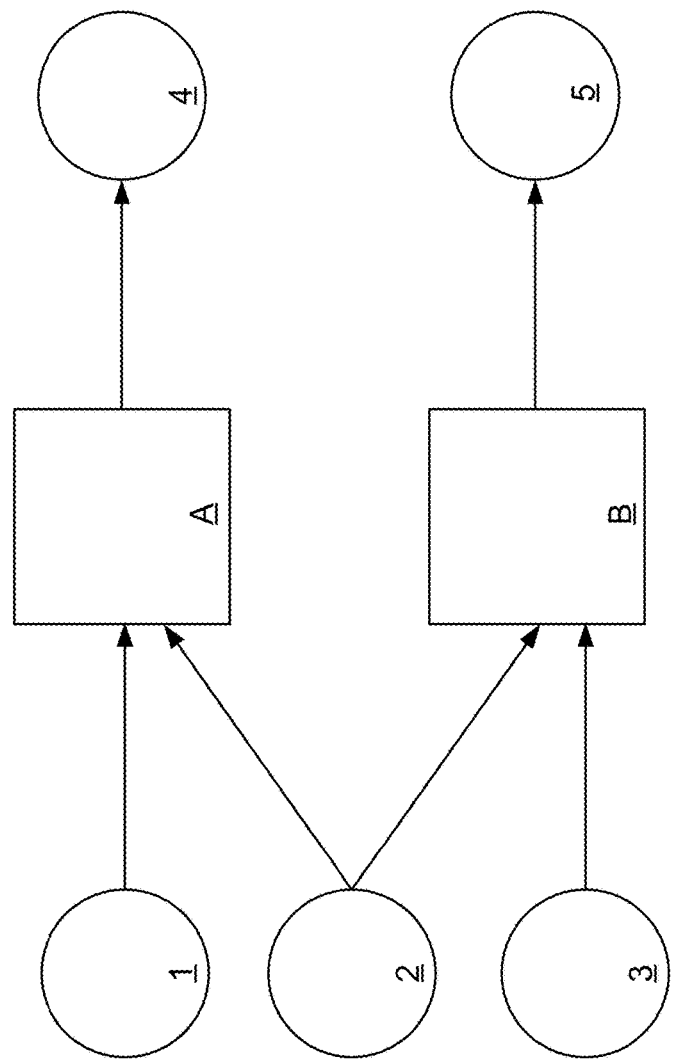
FIG. 8 is a schematic diagram of two chemical reactions, according to an example embodiment.

FIG. 8 depicts a chemical reaction 'A' and a chemical reaction 'B.' A precursor '1' may be a precursor of the chemical reaction 'A.' A precursor '2' may be a precursor of both the chemical reaction 'A' and the chemical reaction 'B'. A precursor '3' may be a precursor of the chemical reaction 'B.' The chemical reaction 'A' may yield a reaction product '4' and the chemical reaction 'B' may yield a reaction product '5.'

Initially, the computing system 100 may simulate the progress of the chemical reactions 'A' and 'B' as a group for at least the reason that the chemical reactions 'A' and 'B' share the precursor '2.' The chemical reaction 'A' may consume the precursor '2' at a rate defined by $dQ_{A2}/dt = -k_A * Q_1 * Q_2$ where $k_A$ is a rate constant, $Q_1$ is a quantity or concentration of the precursor '1,', and $Q_2$ is a quantity or concentration of the precursor '2.' The chemical reaction 'B' may consume the precursor '2' at a rate defined by $dQ_{B2}/dt = -k_B * Q_2 * Q_3$ where $k_B$ is a rate constant and $Q_3$ is a quantity or concentration of the precursor '3.' At some point during the simulation, the computing system 100 may determine that $(dQ_{B2}/dt)/(dQ_{A2}/dt)$ is greater than a predetermined threshold ratio. In some examples, the threshold ratio may be 100 or 10, but other examples are possible. $dQ_{A2}/dt$ might decrease substantially because $Q_1$ has become very low, for example. Once $(dQ_{B2}/dt)/(dQ_{A2}/dt)$ is determined to be greater than the threshold value, the computing system 100 may begin simulating the reaction 'B' without simulating the reaction 'A.' Based on $(dQ_{B2}/dt)/(dQ_{A2}/dt)$ exceeding the threshold value, the effect of the chemical reaction 'A' on $Q_2$ may be ignored as negligible. This technique may involve trading some accuracy in the calculated quantity $Q_2$ in return for shortening the time of the simulation.

Figure 9:
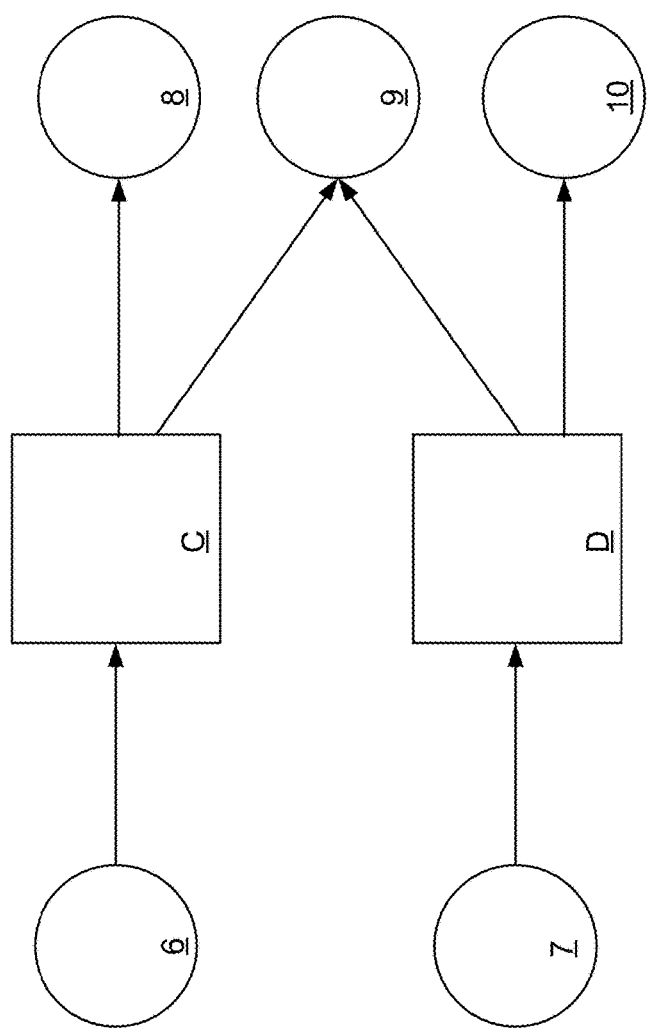
FIG. 9 is a schematic diagram of two chemical reactions, according to an example embodiment.

FIG. 9 depicts a chemical reaction 'C' and a chemical reaction 'D.' A precursor '6' may be a precursor of the chemical reaction 'C.' A precursor '7' may be a precursor of the chemical reaction 'D.' The chemical reaction 'C' may yield reaction products '8' and '9,' and the chemical reaction 'D' may yield a reaction product '10.'

The chemical reaction 'C' may yield the reaction product '9' at a rate defined by $dQ_{C9}/dt = k_C * Q_6$ where $k_C$ is a rate constant and $Q_6$ is a quantity or concentration of the precursor '6.' The chemical reaction 'D' may yield the reaction product '9' at a rate defined by $dQ_{D9}/dt = k_D * Q_7$ where $k_D$ is a rate constant and $Q_7$ is a quantity or concentration of the precursor '7.' At some point during the simulation, the computing system 100 may determine that $(dQ_{D9}/dt)/(dQ_{C9}/dt)$ is greater than a predetermined threshold ratio. In some examples, the threshold ratio may be 100 or 10, but other examples are possible. $dQ_{C9}/dt$ might decrease substantially because $Q_6$ has become very low, for example. Once $(dQ_{D9}/dt)/(dQ_{C9}/dt)$ is determined to be greater than the threshold value, the computing system 100 may begin simulating the reaction 'D' without simulating the reaction 'C.' Based on $(dQ_{D9}/dt)/(dQ_{C9}/dt)$ exceeding the threshold value, the effect of the chemical reaction 'C' on $Q_9$ may be ignored as negligible. This technique may involve trading some accuracy in the calculated quantity $Q_9$ in return for shortening the time of the simulation.

In some examples, the calculated quantity of a particular precursor might be of interest. The particular precursor might be a precursor for both a first chemical reaction and a second chemical reaction. At some point in the simulation, the computing system 100 may determine a first rate at which the first reaction consumes the particular precursor and a second rate at which the second reaction consumes the particular precursor. If the computing system 100 determines that a ratio of the first rate to the second rate exceeds a threshold level, the computing system 100 may perform one or more iterations of the simulations without accounting for the second reaction. That is, based on the first reaction consuming the particular precursor much more quickly than the second reaction, the computing system 100 may "skip" simulating the second reaction for one or more iterations. For example, the second reaction might only be accounted for on every fifth iteration. In other examples, the second reaction may simply be ignored and not included in further simulation. Other examples are possible.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are contemplated herein.

What is claimed is:

1. A method comprising:
   identifying a first group of one or more chemical reactions and a second group of one or more chemical reactions, wherein the first group of one or more chemical reactions use a first set of one or more precursors to produce a first set of one or more reaction products and the second group of one or more chemical reactions use a second set of one or more precursors to produce a second set of one or more reaction products, such that (a) no precursor in the first set of one or more precursors is also in the second set of one or more precursors, (b) no reaction product in the first set of one or more reaction products is also a precursor in the second set of one or more precursors, and (c) no reaction product in the second set of one or more reaction products is also a precursor in the first set of one or more precursors;

based on reaction kinetics of the one or more chemical reactions of the first group and initial respective quantities of the one or more precursors in the first set of one or more precursors, executing a first processing thread to iteratively calculate subsequent respective quantities of the one or more precursors in the first set of one or more precursors; and based on reaction kinetics of the one or more chemical reactions of the second group and initial respective quantities of the one or more precursors in the second set of one or more precursors, executing a second processing thread to iteratively calculate subsequent respective quantities of the one or more precursors in the second set of one or more precursors, wherein the first processing thread and the second processing thread are executed contemporaneously, wherein the first group of one or more chemical reactions comprises a first chemical reaction, a second chemical reaction, and a third chemical reaction, wherein the first set of one or more precursors comprises a first precursor, a second precursor, and a third precursor, wherein the first precursor is a precursor of the first chemical reaction and a precursor of the second chemical reaction, wherein the second precursor is a precursor of the second chemical reaction, and wherein the third precursor is a precursor of the second chemical reaction and a precursor of the third chemical reaction, the method further comprising:
      determining that an amount remaining of the second precursor is less than a threshold amount by executing the first processing thread;
      iteratively calculating further subsequent quantities of the third precursor by executing a third processing thread; and
      contemporaneous with the execution of the third processing thread, continuing to execute the first processing thread to iteratively calculate further subsequent quantities of the first precursor.

2. The method of claim 1, further comprising:
   executing the first processing thread to iteratively calculate respective quantities of the one or more reaction products in the first set of reaction products; and
   executing the second processing thread to iteratively calculate respective quantities of the one or more reaction products in the second set of reaction products.

3. The method of claim 1, wherein the first processing thread is executed by a first processor of a computing device and the second processing thread is executed by a second processor of the computing device.

4. The method of claim 1, wherein the first processing thread is executed by a processor of a first computing device and the second processing thread is executed by a processor of a second computing device.

5. The method of claim 1,
   wherein the first group of one or more chemical reactions comprises a fourth chemical reaction and one or more fifth chemical reactions, and
   wherein the first set of one or more precursors comprises a particular precursor that is a precursor of the fourth chemical reaction, the method further comprising:

executing the first processing thread to determine that the fourth chemical reaction has become decoupled from the one or more fifth chemical reactions; and in response to determining that the fourth chemical reaction has become decoupled from the one or more fifth chemical reactions, executing a fourth processing thread to iteratively calculate subsequent quantities of the particular precursor.

6. The method of claim 1, further comprising:

determining that the first group of one or more chemical reactions has become recoupled to the second group of one or more chemical reactions; and in response to determining that the first group of one or more chemical reactions has become recoupled to the second group of one or more chemical reactions, executing a single processing thread to iteratively calculate subsequent respective quantities of both the first set of one or more precursors and the second set of one or more precursors.

7. The method of claim 1, further comprising:

determining that an amount of the second precursor is greater than the threshold amount; and in response to determining that the amount of the second precursor is greater than the threshold amount, executing a single processing thread to iteratively calculate subsequent respective quantities of both (a) the second precursor and (b) the first precursor or the third precursor.

8. The method of claim 1, further comprising:

prior to executing the first processing thread and executing the second processing thread, receiving input indicating (a) the initial respective quantities of the one or more precursors in the first set and (b) the initial respective quantities of the one or more precursors in the second set.

9. The method of claim 1, wherein executing the first processing thread comprises:

based on the reaction kinetics of the one or more chemical reactions of the first group and the initial respective quantities of the one or more precursors in the first set, assigning respective probabilities to the one or more chemical reactions of the first group, wherein the subsequent respective quantities of the one or more precursors in the first set are calculated by comparing a randomly generated number to at least one of the respective probabilities to determine which of the one or more chemical reactions of the first group occurs next.

10. The method of claim 1, wherein executing the first processing thread comprises:

based on the reaction kinetics of the one or more chemical reactions of the first group and the initial respective quantities of the one or more precursors in the first set, determining respective reaction rates for each of the one or more chemical reactions of the first group, wherein the subsequent respective quantities of the one or more precursors in the first set are calculated by using the determined respective reaction rates.

11. One or more units of non-transitory computer readable media storing instructions that, when executed by a computing system, cause the computing system to perform functions comprising:

identifying a first group of one or more chemical reactions and a second group of one or more chemical reactions, wherein the first group of one or more chemical reactions use a first set of one or more precursors to produce a first set of one or more reaction products and the second group of one or more chemical reactions use a second set of one or more precursors to produce a second set of one or more reaction products, such that (a) no precursor in the first set of one or more precursors is also in the second set of one or more precursors, (b) no reaction product in the first set of one or more reaction products is also a precursor in the second set of one or more precursors, and (c) no reaction product in the second set of one or more reaction products is also a precursor in the first set of one or more precursors;

based on reaction kinetics of the one or more chemical reactions of the first group and initial respective quantities of the one or more precursors in the first set of one or more precursors, executing a first processing thread to iteratively calculate subsequent respective quantities of the one or more precursors in the first set of one or more precursors; and based on reaction kinetics of the one or more chemical reactions of the second group and initial respective quantities of the one or more precursors in the second set of one or more precursors, executing a second processing thread to iteratively calculate subsequent respective quantities of the one or more precursors in the second set of one or more precursors, wherein the first processing thread and the second processing thread are executed contemporaneously, wherein the first group of one or more chemical reactions comprises a first chemical reaction, a second chemical reaction, and a third chemical reaction, wherein the first set of one or more precursors comprises a first precursor, a second precursor, and a third precursor, wherein the first precursor is a precursor of the first chemical reaction and a precursor of the second chemical reaction, wherein the second precursor is a precursor of the second chemical reaction, and wherein the third precursor is a precursor of the second chemical reaction and a precursor of the third chemical reaction, the functions further comprising:

determining that an amount remaining of the second precursor is less than a threshold amount by executing the first processing thread;

iteratively calculating further subsequent quantities of the third precursor by executing a third processing thread; and contemporaneous with the execution of the third processing thread, continuing to execute the first processing thread to iteratively calculate further subsequent quantities of the first precursor.

12. The one or more units of non-transitory computer readable media of claim 11, wherein the first group of one or more chemical reactions comprises a fourth chemical reaction and one or more fifth chemical reactions, and wherein the first set of one or more precursors comprises a particular precursor that is a precursor of the fourth chemical reaction, the functions further comprising:

executing the first processing thread to determine that the fourth chemical reaction has become decoupled from the one or more fifth chemical reactions; and in response to determining that the fourth chemical reaction has become decoupled from the one or more fifth chemical reactions, executing a fourth processing thread to iteratively calculate subsequent quantities of the particular precursor.

13. The one or more units of non-transitory computer readable media of claim 12, the functions further comprising:
  determining that the first group of one or more chemical reactions has become recoupled to the second group of one or more chemical reactions; and
  in response to determining that the first group of one or more chemical reactions has become recoupled to the second group of one or more chemical reactions, executing a single processing thread to iteratively calculate subsequent respective quantities of both the first set of one or more precursors and the second set of one or more precursors.

14. The one or more units of non-transitory computer readable media of claim 11, the functions further comprising:
  executing the first processing thread to iteratively calculate respective quantities of the one or more reaction products in the first set of reaction products; and
  executing the second processing thread to iteratively calculate respective quantities of the one or more reaction products in the second set of reaction products.

15. The one or more units of non-transitory computer readable media of claim 11, wherein the first processing thread is executed by a first processor of a computing device and the second processing thread is executed by a second processor of the computing device.

16. The one or more units of non-transitory computer readable media of claim 11, wherein the first processing thread is executed by a processor of a first computing device and the second processing thread is executed by a processor of a second computing device.

17. The one or more units of non-transitory computer readable media of claim 11, the functions further comprising:
  determining that an amount of the second precursor is greater than the threshold amount; and
  in response to determining that the amount of the second precursor is greater than the threshold amount, executing a single processing thread to iteratively calculate subsequent respective quantities of both (a) the second precursor and (b) the first precursor or the third precursor.

18. A computing system comprising:
  one or more processors; and
  one or more memory units storing instructions that, when executed by the one or more processors, cause the computing system to perform functions comprising:
    identifying a first group of one or more chemical reactions and a second group of one or more chemical reactions, wherein the first group of one or more chemical reactions use a first set of one or more precursors to produce a first set of one or more reaction products and the second group of one or more chemical reactions use a second set of one or more precursors to produce a second set of one or more reaction products, such that (a) no precursor in the first set of one or more precursors is also in the second set of one or more precursors, (b) no reaction product in the first set of one or more reaction products is also a precursor in the second set of one or more precursors, and (c) no reaction product in the second set of one or more reaction products is also a precursor in the first set of one or more precursors;
    based on reaction kinetics of the one or more chemical reactions of the first group and initial respective quantities of the one or more precursors in the first set of one or more precursors, executing a first processing thread to iteratively calculate subsequent respective quantities of the one or more precursors in the first set of one or more precursors; and
    based on reaction kinetics of the one or more chemical reactions of the second group and initial respective quantities of the one or more precursors in the second set of one or more precursors, executing a second processing thread to iteratively calculate subsequent respective quantities of the one or more precursors in the second set of one or more precursors,
    wherein the first processing thread and the second processing thread are executed contemporaneously,
  wherein the first group of one or more chemical reactions comprises a first chemical reaction, a second chemical reaction, and a third chemical reaction,
  wherein the first set of one or more precursors comprises a first precursor, a second precursor, and a third precursor,
  wherein the first precursor is a precursor of the first chemical reaction and a precursor of the second chemical reaction,
  wherein the second precursor is a precursor of the second chemical reaction, and
  wherein the third precursor is a precursor of the second chemical reaction and a precursor of the third chemical reaction, the functions further comprising:
    determining that an amount remaining of the second precursor is less than a threshold amount by executing the first processing thread;
    iteratively calculating further subsequent quantities of the third precursor by executing a third processing thread; and
    contemporaneous with the execution of the third processing thread, continuing to execute the first processing thread to iteratively calculate further subsequent quantities of the first precursor.

19. The computing system of claim 18,
  wherein the computing system comprises a first computing device and a second computing device,
  wherein the first computing device comprises a first processor of the one or more processors and the second computing device comprises a second processor of the one or more processors, and
  wherein the first processing thread is executed by the first processor and the second processing thread is executed by the second processor.

20. The computing system of claim 18,
  wherein the one or more processors comprise a first processor and a second processor, and
  wherein the first processing thread is executed by the first processor and the second processing thread is executed by the second processor.

* * * * *